United States Patent [19]

Metcalf

[11] 4,043,332

[45] Aug. 23, 1977

[54] CONSTANT FLOW RATE LIQUID MEDICAMENT ADMINISTERING DEVICE

[75] Inventor: Harold J. Metcalf, Stony Brook, N.Y.

[73] Assignees: Nathan Blumberg, Smithtown; Public Systems Research, Inc.; Harold J. Metcalf, both of Stony Brook, all of N.Y.; part interest to each

[21] Appl. No.: 577,294

[22] Filed: May 14, 1975

[51] Int. Cl.² .............................................. A61M 5/00
[52] U.S. Cl. .................. 128/214 E; 73/271; 128/DIG. 13; 128/DIG. 12; 137/225
[58] Field of Search .......... 128/214 F, 214 E, 214 R, 128/214.2, 280, DIG. 12, DIG. 13, 214 C; 137/225, 505.13, 510, 525, 528; 222/71, 20, 19, 56; 73/271, 249

[56] References Cited

U.S. PATENT DOCUMENTS

| | | | |
|---|---|---|---|
| 2,068,578 | 1/1937 | Stronach | 272/79 C |
| 2,766,907 | 10/1956 | Wallace | 128/214 F X |
| 3,034,504 | 5/1962 | Winsor et al. | 128/214.2 |
| 3,039,399 | 6/1962 | Everett | 128/214 R |
| 3,123,094 | 3/1964 | Toschkoff | 137/505.13 |
| 3,468,308 | 9/1969 | Bierman | 128/DIG. 12 |
| 3,563,090 | 2/1971 | Deltour | 128/214 E |
| 3,890,968 | 6/1975 | Pierce et al. | 128/214 E |

Primary Examiner—Richard C. Pinkham
Assistant Examiner—William R. Browne
Attorney, Agent, or Firm—Kirschstein, Kirschstein, Ottinger & Frank

[57] ABSTRACT

A constant flow rate liquid medicament administering device which includes a container having a liquid medicament therein. The liquid medicament is fed under pressure to a constant output flow rate regulator that is operated by a drop in pressure between its inlet and outlet. The liquid leaving the regulator under reduced pressure and at a constant flow rate independent of entering pressure is led to a drip chamber in which any gas entrapped in the liquid is released so as to prevent introduction of gas into a patient. The drip rate in the chamber furnishes a rough visual indication of flow rate, the regulator being adjustable to secure any desired rate. Either before or after passage of the liquid through the drip chamber, the liquid is passed through a flow rate indicator which more accurately provides an instantaneous reading of flow rate. Finally, the liquid is led to an administering implement for introducing the liquid into a patient at a constant flow rate.

6 Claims, 5 Drawing Figures

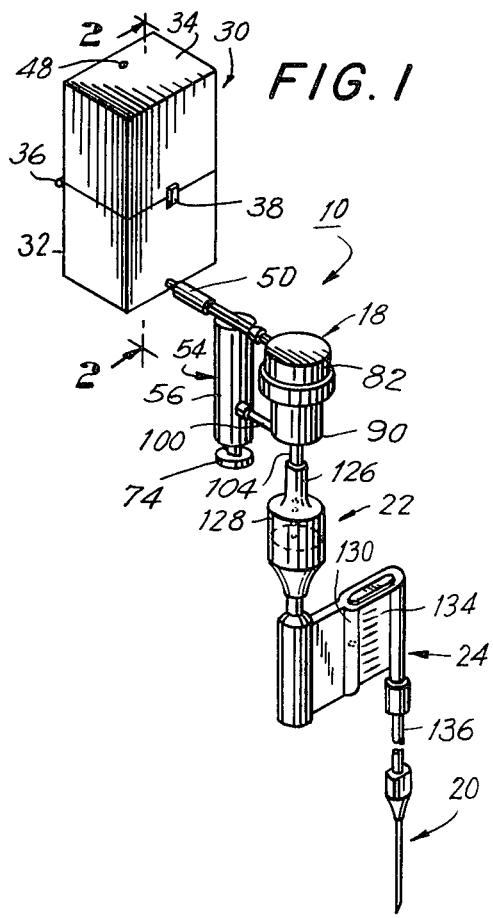
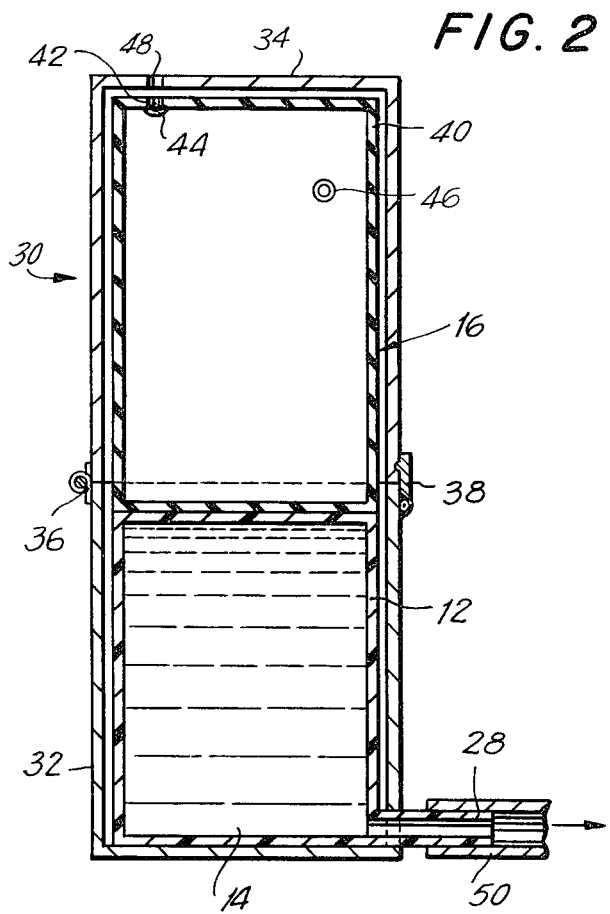
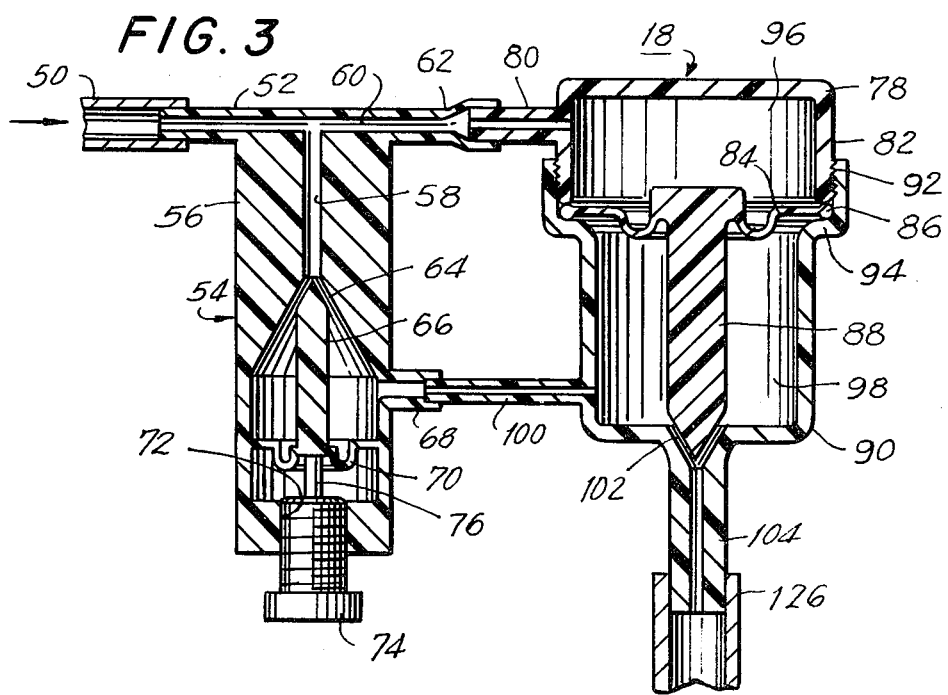

CONSTANT FLOW RATE LIQUID MEDICAMENT ADMINISTERING DEVICE

BACKGROUND OF THE INVENTION

1. Field of the Invention

System for furnishing a liquid medicament to a patient at a constant flow rate. 2. Description of the Prior Art The system of the present invention is utilized in the treatment of human and animal patients. It is employed to supply a liquid to a patient. Such liquid has been described herein as a "medicament", the term being used in its broadest possible sense to include all liquids that are to be supplied for any reason whatsoever. For instance, such liquids include liquids that are introduced intravenously, these including, by way of example, blood, saline solutions, glucose solutions and solutions including pharmaceuticals. Medicament liquids also include liquids that are administered by perfusion, both intravenously administered liquids and liquids administered by perfusion being introduced into the body parenterally as with the use of a hypodermic needle. Liquid medicaments administered by the present system also include liquid medicaments that are introduced into the stomach, usually by a tube threaded through the nose and down the gullet, or into the colon with the aid of a bone.

Until the present time, the most widely utilized system for administration of liquid medicaments constituted a limp bag frequently purchased with liquid medicament therein in sterile condition which was supported at an elevated position with respect to the patient and was connected through a conduit to a means for introducing the liquid into the patient, e.g. a nasal/stomach tube, a hypodermic needle or a bone. Some arrangement was included to adjust the flow of liquid. For example, an adjustable clip was applied to the exterior of a flexible conduit that ran from the bag to the patient. This, of course, was extremely crude and was subject to a considerable variation in the rate of flow of the liquid medicament into the patient. This rate depended upon external considerations chief among which was the setting of flow control and the height of the liquid in the bag. Obviously, the rate of flow was a function of the pressure of the liquid at the point of administration to the patient and this, in turn, was a function of the difference in elevation between the point of administration and the level of the liquid in the bag. As the level dropped with consumption of liquid, the pressure at the point of administration dropped and, with it, the flow rate was reduced. Of course, the setting of the regulator also was a factor, but at least this was controllable, even through coarsely. It also was customary to include in the line running from the bag to the patient a drip chamber which had two functions. One was to observe the rate of flow by either counting the number of drops per unit of time observed in the drip chamber, and the other was to liberate gas that might be present in the liquid so as to prevent its introduction into the patient. The drip chamber conventionally was upstream of the flow regulator clip.

The art has been aware of the problem of change of pressure head of the liquid medicament and has made many efforts to overcome the problem of variable flow rate created thereby. The art also has been aware of the fact that bags such as described above tend to inhibit portability of the administering device. Various alternate arrangements have been suggested. Thus, it has been proposed to pressurize the liquid in the bag by either an external or an internal gas-filled bladder which transmitted the pressure in such bladder to the liquid in the bag, hopefully thereby maintaining a constant pressure on the liquid and therefore a constant flow rate at the point of administration. However, this was not the result because as the bladder expanded, the pressure of the gas therein dropped by virtue of Boyle's Law. Even using a large bladder and a small bag, the drop essentially and appreciably affected flow rate. Still further, due to changes in ambient temperature which were not always controllable, particularly when administration of the liquid medicament was outside of a hospital, a pressure fluctuation ensued by virtue of Charles' Law which resulted in an additional change in flow rate that could either be additive or subtractive to the change resulting from variation in volume.

Other proposals have been made to pressurize a liquid medicament in a bag by weights, rollers and springs, but in each instance there invariably was a variation in flow rate that took place as the liquid medicament was discharged from the bag.

Furthermore, it has been suggested to use flow rate controls. One of these was mentioned previously, to wit, an adjustable constrictive clamp. Another one which appears in the patent literature is a porous plug. Both of these can be used to provide a constant rate of flow but only if the pressure head of the liquid entering the control is constant. As soon as the pressure varies, as essentially it must due to various physical factors, the rate of flow changes in response to such variation.

Therefore, until the present there has been no liquid medicament administering device available, either commercially or in patent literature, which will introduce a liquid medicament into a patient at a constant rate of flow which is independent of variations in pressure head of the liquid medicament and idependent of back pressure variations at the delivery site. Furthermore, the physical constructions of the various liquid medicament administering devices heretofore available or proposed have been relatively cumbersome or complex, costly, or difficult to service, sterilize or maintain sterile.

An additional disadvantage of presently available devices of the character described is that they require monitoring by a nurse or other suitable attendant to insure that their flow rate is maintained at least approximately near the level prescribed by a doctor. Not all nurses are assiduous in their duties, so that a patient can be improperly treated for many hours with all of the consequent problems.

SUMMARY OF THE INVENTION

1. Purposes of the Invention

It is an object of the present invention to provide a unique liquid medicament administering device which is not subject to any of the foregoing disadvantages.

It is another object of the invention to provide a device of the character described which will supply a liquid medicament to a patient at a substantially constant flow rate which essentially is independent of the pressure of the liquid medicament.

It is another object of the invention to provide a device of the character described including a container for the liquid medicament and a constant output flow rate regulator wherein the regulator is operated by a drop in pressure across the same and wherein the flow rate is independent of the entering pressure.

It is another object of the invention to provide a device of the character described which further includes a drip chamber for eliminating any gas that may be present in the liquid medicament, a flow rate measuring device so as to avoid the necessity of observing the drip rate and so as also to be able immediately to secure an indication of the then-prevailing flow rate, and which further includes an element for introduction to a patient so as to administer the liquid medicament to the patient.

It is another object of the invention to provide a device of the character described which further includes an alarm or alerting means that automatically will provide a signal or the like that flow of the liquid to the patient has been stopped so as to immediately provide succor.

It is another object of the invention to provide a device of the character described which constitutes relatively few and simple parts, is inexpensive to manufacture, is easy to clean and sterilize, is easy to purge and will maintain the liquid medicament passed therethrough in sterile condition.

It is another object of the invention to provide a device of the character described which is portable, non-electric and light in weight.

It is another object of the invention to provide a device of the character described which can handle liquids over the entire range of viscosities and specific gravities that are employed for administration to patients.

It is another object of the invention to provide a device of the character described which can be used wiith equal ease for all modes of administration such as intravenous, perfusion and routing to the digestive tract.

Other objects of the invention in part will be obvious and in part will be pointed out hereinafter.

2. Brief Description of the Invention

The device of the present invention is useful for all modes of administration of liquid medicaments to patients, be they human or animal. Thus, it can be employed for intravenous administration, for perfusion and for routing of liquids to the digestive tract.

Essentially, the device includes four necessary elements and, desirably, includes three further elements.

The first necessary element constitutes a container for a liquid medicament, for example, a limp transparent plastic bag such as is furnished to hospitals and the like and which has therein a suitable liquid medicament. A typical medicament is a saline solution, a glucose solution or a solution containing pharmaceuticals. The container also may be rigid or semi-rigid as, for example, bottles in which whole blood or blood fractions are shipped.

The second necessary element constitutes an arrangement for pressurizing the liquid medicament. Preferably, the arrangement pressurizes the liquid medicament within the container for the medicament, although this is not absolutely necessary. For example, the pressurization can be achieved with the aid of a pump. However, it is desirable not to use such a type of means because power has to be supplied to drive it and it is most desirable that the device independent of a source of power, particularly of a source of power which must supply a substantial amount of energy such, for instance, as a battery or an electrical outlet, inasmuch as the device in its preferred form is portable and should be light in weight. For example, devices of the character under consideration frequently are secured to a hospital bed and must be moved along with the bed so that they cannot be connected to an electrical outlet. The devices also may be attached to a stretcher and here, too, an electrical outlet is not a proper source for supplying power, nor would the ambulance attendants or stretcher bearers relish the thought of carrying about a battery along with the patient. Moreover, these devices may be furnished in the form of emergency kits and may stand about for some period of time during which a battery can become ineffective. It is best that such a kit be fully self-contained or at least be capable of ready charging for pressurization as the need arises. One suitable and preferred arrangement for pressurization is a bladder which can be filled with gas, the bladder being in physical contact with a limp container for the liquid medicament so that the liquid medicament likewise is placed under pressure. The pressurization means need not maintain a constant pressure in the liquid. Indeed, if it could and if that pressure remained constant despite changing ambient conditions, the present invention would not be necessary because then the flow rate could easily be maintained constant. However, it is not desirable to use a pressurizing means with extreme fluctuations in pressure. Ergo, the pressurization means used in the present invention should pressurize the liquid medicament but, desirably, should not have a fluctuation pressure of more than approximately 300%.

The third necessary element is a constant flow rate regulator which is operated by a drop in pressure between its inlet and outlet. One of the reasons that the pressurizing means is included in the present device is that the pressure thus created in the liquid medicament upstream of the regulator is utilized by the regulator to achieve a constant flow rate for its output. The reduced pressure at the outlet of the regulator is sufficient to pass the liquid through subsequent elements in the device, very little pressure being required for this purpose.

The fourth necessary element is an implement for coupling the device to a patient. Typical implements include a hypodermic needle for intravenous application or for perfusion, and a tube and/or bone for introduction of the liquid into the digestive tract.

The first further desirable element is a drip chamber which has as one function the release of entrapped gas in the liquid medicament and as another function a visual indication of rate of flow. The drop chamber is principally desirable for gas release. Its rate of flow function is desirable because hospital personnel and the like are accustomed to seeing a drip chamber and to mentally evaluating rate of flow by visual observation thereof. However, the rate of flow indication is somewhat subjective and is inaccurate unless measured against time.

Therefore, there desirably is included in the present device a second further element which constitutes a rate of flow indicator such, for instance, as the well-known rotometer in which a ball floats in a tapered transparent tube through which the liquid medicament passes so that the position of the ball lengthwise of the tube is a direct function of the rate of flow.

The third further desirable element is an alarm, i.e. signaling mechanism, which furnishes an indication when the flow rate is either too high or too low. Too low a flow rate obviously is undesirable because it constitutes, in effect, exhaustion of the liquid medicament or a breakdown in the device which inhibits further administration of the liquid to the patient. Too high a flow rate also is undesirable because it, too, may be a result of a breakdown of the device and, in any event, may be dangerous because rapid introduction of any liquid medicament into the body of a patient can be damaging and even fatal. This last element conveniently is associated with the flow measuring device and, for example, may constitute two position-indicating means for the ball such as an electrical contact or a light beam, one at one extreme position of the ball and the other at the other extreme position of the ball.

The invention consists in the features of construction, combination of elements and arrangement of parts which will be exemplified in the device hereinafter described and of which the scope of application will be indicated in the appended claims.

BRIEF DESCRIPTION OF THE DRAWINGS

In the accompanying drawings in which are shown various possible embodiments of the invention:

FIG. 1 is a perspective view of a constant flow rate liquid medicament administering device constructed in accordance with and embodying the present invention;

FIG. 2 is an enlarged sectional view taken substantially along the line 2—2 of FIG. 1;

FIG. 3 is a central vertical sectional view through the constant flow rate regulator forming one of the elements of the device shown in FIG. 1;

PREFERRED EMBODIMENTS OF THE INVENTION

Figure 4:
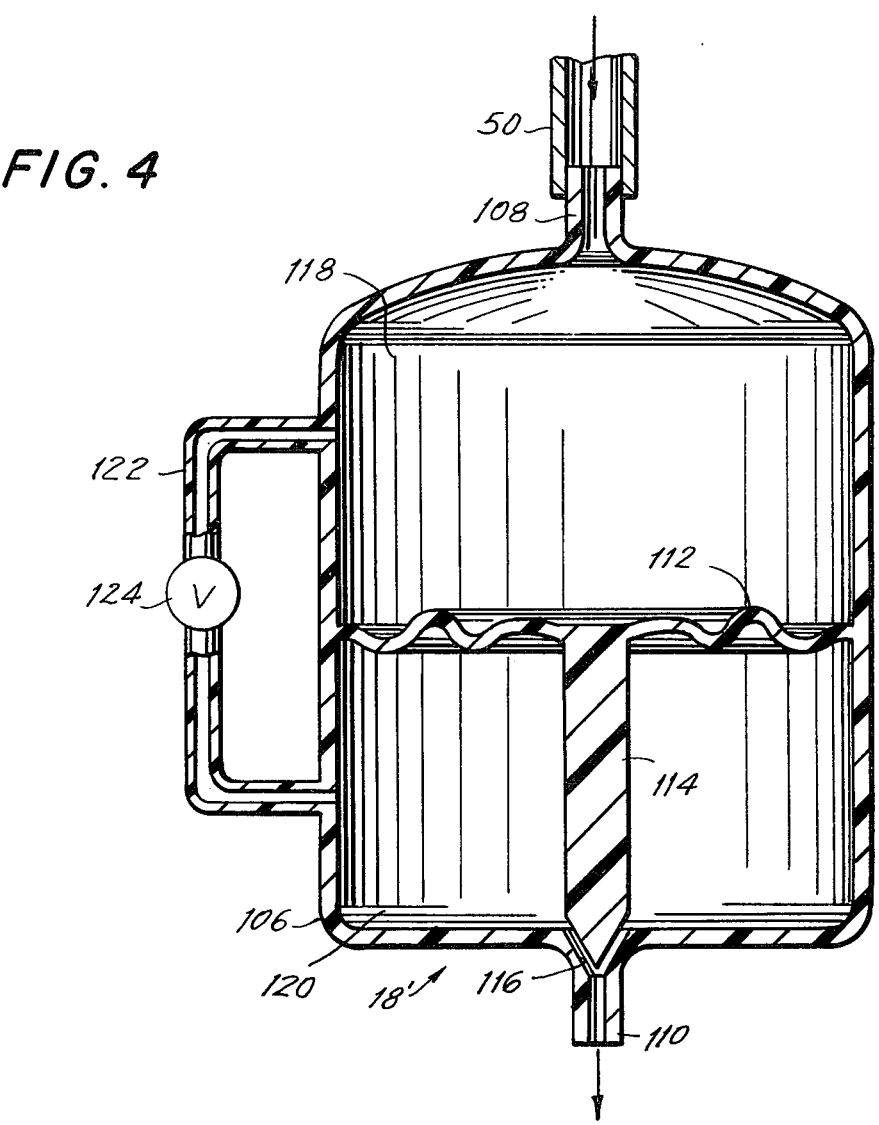
FIG. 4 is a view similar to FIG. 3 of a modified form of constant flow rate regulator.

Referring now in detail to the drawings, and more particularly to FIGS. 1-3, the reference numeral 10 denotes a device which forms the subject of the present invention, the same constituting an apparatus for administering a liquid medicament at a constant rate of flow to a patient. This device is so constructed that a selectable constant rate of flow of liquid medicament will be delivered regardless of a reasonably wide latitude of pressure under which the liquid medicament is placed as by gravitational, fluid or mechanical means. Said device is composed of seven principal elements of which four are essential and three are optional but desirable, the desirability being of various degrees.

The four essential elements are a container 12 in which a liquid medicament 14 is disposed, a pressurizing means 16 the sole function of which is to place the liquid contents of the container under pressure, a constant flow rate regulator 18, and an implement 20 for coupling the device to a patient.

The three optional desirable elements are a drip chamber 22, a flow measuring device 24, and an alarm signaling mechanism 26.

The pressurizing means is arranged as will be described in greater detail hereinafter so that when operative it imparts a suitable pressure to the liquid 14 in the container 12. The container 12, the constant flow rate regulator 18, the drip chamber 14, the flow measuring device 24 and the implement 20 are connected in series, the desired sequence being as illustrated, and connection being effected either by direct coupling of one element to another or by interposition of conduits which are shown in FIG. 1.

It will be appreciated from the description of the device 10 which follows that the same is capable of efficiently delivering a liquid medicament to a patient in any mode that might be needed and will do so with stability, repeatability and precision. The clinical characteristics of said device are such that the sterility of the liquid medicament administered to the patient is preserved. Such liquid will not come into contact with exposed or manually handled surfaces. The rate of flow of the liquid administered varies by less than 5% over a complete cycle of use from the start of delivery from a full container to the termination of delivery when the container is empty and, as a matter of practice, the variation in the delivery rate of the liquid medicament has been under 1% over such period. When the aforesaid delivery rates are considered, they are considered on a long-term basis. Short-term fluctuations are inevitable, but they are not detectable over a period of as little as one minute. Moreover, it will be appreciated as the description proceeds that the device will protect the patient in the event of even the most unlikely accident or misuse thereof. There is no way that a patient can be suddenly injected with large quantities of liquid or with any quantity of gas. The device is fail-safe under all except the most unusual of circumstances such, for instance, as deliberate misuse or mishandling.

In addition to the foregoing, the device is non-electric and portable as well as being lightweight. This makes it suitable for ambulatory and otherwise mobile patients. It also facilitates moving a bed between rooms or to a diagnostic or treatment facility. No battery is employed which would make In addition to the foregoing, the device is non-electric and portable as well as being lightweight. This makes it suitable for ambulatory and otherwise mobile patients. It also facilitates moving a bed between rooms or to a diagnostic or treatment facility. No battery is employed which would make the device impractical because of its weight or which would make the provision of a stand-by kit infeasible.

It further will be appreciated that the new device will conform to hospital routine easily without special handling because it looks like, acts like and is handled like equipment with which hospital personnel are familiar. Moreover, the device is compatible with existing liquid medicament administering apparatus. The device is so constructed that it can handle all liquids likely to be encountered during the treatment of a patient despite differences in viscosity and specific gravity. Nor does the precision of the device in obtaining a constant rate of delivery of the liquid depend upon the properties of the liquid medicament. It can handle liquids whose specific gravity varies from as low as 0.8 to 1.2 and whose viscosity is anywhere between 1 and 2.5 centipoises. The sundry components of the various elements are designed to be manufactured and assembled inexpensively and readily and to be susceptible to sterilization.

The system illustrated has been specifically designed for use with a container 12 of a limp flexible material such as a flexible synthetic plastic. A typical such container is a flexible I-V bag of the type sold by Travenol Corp., although, as will be fully realized from the following description, the present invention also can be used with rigid or semi-rigid containers, this being exemplified by the bottles in which blood and blood fractions currently are available.

Each of the elements now will be described in detail.

The container 12 for the liquid medicament 14 is, in the illustrated form of the invention, in the configuration of a bag such, for instance, as the usual Travenol bag and is made from a limp plastic material which usually is transparent or translucent. The ability of the bag to pass light is not a factor in connection with the present invention inasmuch as the bag will either be full when treatment starts or empty when the entire contents hve been discharged. Conventionally, the bag is constituted of two flat plastic panels which are connected to each other as by welding along their peripheries. Although not shown in the drawings, the bag is furnished with a fill opening which is closed by the manufacturer and filler of the bag in order to keep the liquid medicament sterile. The bag, further, is provided with an outlet 28. In FIG. 2, in which the bag is shown in section, the same being filled, the configuration of the bag is not that of a flat bag but, rather, of a filled bag which has been placed in a receptacle, the bag tending to conform to the shape of that portion of the receptacle occupied by the bag.

To use the bag, there is provided a receptacle 30. Conveniently, this is of rectanguloid shape and includes a deep tray 32 and a deep cover 34 joined by a hinge 36 at one face and a latch 38 at the opposite face. The tray is designed to receive the bag and, again, as illustrated, the tray is deep enough to fully receive the filled bag with an excess volume at the top of the tray. Thus, the top of the tray and the cover are empty when only the bag is located in the receptacle.

Also disposed within the receptacle is a gas bladder 40. The bladder 40 is shaped to be nicely received within the empty space aforementioned when the bladder is filled with a gas under just enough pressure to keep it inflated but not expanded. The bladder is made from an elastomeric material such, for instance, as a natural or synthetic rubber and is thin enough so that when gas is injected into the same through an inlet 42 the bladder will enlarge unless constrained. A check valve 44 is located in the inside of the bag over the inlet opening. The valve permits entry of gas under pressure but not exit therefrom unless the valve is opened by insertion of a slender instrument into the inlet. The bladder further includes a safety valve 46. The bladder is charged with a gas under pressure after the bladder has been inserted in the receptacle, the gas-filling tube penetrating the upper wall of the cover through an opening 48 provided for that purpose.

Initially, the liquid-filled bag is inserted in the receptacle with the outlet 28 extending through an opening formed in the tray, then the bladder, either partially or fully inflated but not yet internally pressurized, is placed over the bag and the cover which, up to this point, has been open, is swung to a closed position and the latch engaged. Now, additional gas under pressure is injected into the gas bladder. Any suitable source of gas can be employed. A typical source is a carbon dioxide cartridge or the oxygen which is available under pressure in a conventional hospital room. Ordinarily, this oxygen is present at about 55 psig. However, care is exercised when charging the bladder not to permit too great a pressure to be built up therein. A desired pressure for the initial charge of gas into the gas bladder is in the range of 7 to 8 psig, although this is not to be considered as a limitation upon the invention — it is merely a guide to a suitable pressure to employ.

The gas bladder 40 constitutes the pressurizing means 16 hereinabove referred to. Because both the gas in the bladder and the liquid in the bag are fluids, and because the gas bladder is fully constrained when pressurized, a wall of the bladder will be in contact with and press against a wall of the bag, so that approximately the same pressure as the gas pressure will prevail within the bag, i.e. the liquid medicament in the bag will be under approximately the same pressure as the gas in the gas bladder. It bears repetition to state that the pressure of the liquid in the bag is not the pressure under which liquid will be administered to the patient. The pressure of said liquid as thus pressurized has as its primary purpose the operation of the constant flow regulator 18 which requires a drop in pressure against the same for correct functioning. A typical drop in pressure across such a regulator is in the vicinity of 3 psi, so that the initial pressure at which liquid is furnished to the flow measuring device will be in the range of 3 to 4 psig. This is not too great a pressure at which to introduce liquid into a patient, bearing in mind that the flow rate is controlled so that the liquid is not allowed to flow freely. Furthermore, of course, when the device 10 is used with a parenteral administering implement 20, there is some resistance to injection of the medicament, so that a 3 to 4 lb. pressure is medically acceptable. Subsequently, the pressure imparted to the liquid medicament will drop as the gas bladder expands, so that there will be a drop in the pressure of the liquid as it enters the constant flow rate regulator 18. However, the drop should not be sufficiently great to prevent an available drop of at least the drop required to operate the regulator. In other words, if the regulator requires a 3 psig drop for proper functioning, the drop in the pressurization of the gas should not be such as to have liquid leave the bag at a pressure less than 3 psig and, indeed, it is preferable that, under the foregoing parameters, the liquid as it is introduced into the regulator have a pressure of not less than about 3.5 psig.

The material from which the receptacle 30 is made can be any suitable self-form-maintaining material which is able to resist the mild pressure imparted to the bag and present in the gas bladder. For convenience, the receptacle can have its tray and cover, and optionally its hinges, injection molded from plastic. Alternatively, the tray and its component parts can be made from metal.

Liquid medicament exiting through the outlet 28 is led by a connecting conduit 50 to the inlet 52 of the constant flow rate regulator 18. Two such regulators have been illustrated herein, one denominated by the reference numeral 18, being shown as to its external configuration in FIG. 1 and its internal configuration in FIG. 3. Another suitable constant flow rate regulator 18' is shown in FIG. 4. The regulator 18 will be described first.

Both regulators are so constructed that if a liquid is introduced into their inlets under pressure, the liquid will leave through their outlets at a reduced pressure at a constant rate of flow.

The regulator 18 includes five parts.

The first part 54 is a control and by-pass. For ease of maintenance and assembly and for low cost, the control and by-pass is molded as a single piece from a synthetic plastic which is capable of sterilization in an autoclave. Said control and by-pass includes a shank 56 having a central passageway 58 that is connected to a by-pass passageway 60 that runs between the inlet 52 and a first flared outlet fitting 62. The central passageway 58 at the end thereof remote from the by-pass passageway 60 runs into a valve seat 64 of conical configuration which is designed to cooperate with the tip of a valve stem 66. Said valve stem and valve seat perform a throttling function which reduces the pressure of the liquid medicament entering the inlet 52 to a lower pressure at which liquid leaves the control and by-pass part at a second flared outlet fitting 68. The base of the valve stem 66 is in one piece with a flexible resilient diaphragm 70.

The shank 56 on the side of the diaphragm opposite from the valve stem 66 includes a female threaded bore 72 in which there is screwed a control stem 74 that constitutes the second part of the control and by-pass 54. Protruding from the control stem is an operating rod 76 that abuts the center of the diaphragm in line with the valve stem 66.

It will be appreciated that by turning the control stem 74, the tip of the valve stem 66 can be made to approach or recede from the valve seat 64 to thereby control the low pressure value of the liquid medicament which will exit from the shank 56 at the second outlet fitting 68. Thus, liquid medicament present at the first outlet fitting 62 is under high pressure, i.e. "high" in the sense that it is the pressure in the liquid medicament resulting from the operation of the pressurizing means 16, whereas the liquid medicament at the second fitting 68 is under a lower pressure, the differential in pressures being that required to operate the regulator 18. By varying the amount of throttling and, hence, the low pressure of the liquid medicament, the rate of flow through the regulator can be adjusted to any desired figure.

A feature of the first part, i.e. the control and by-pass part of the regulator, is the molding of the diaphragm 70 in one piece with said part whereby to avoid the provision of seals, bearings and journals which would increase the difficulty of assembly and sterilization and which would permit contamination that is entirely prevented by the one-piece diaphragm/shank construction.

The third part of the regulator 18 is a high pressure cover 78. This cover has an inlet fitting 80 of tapered configuration designed to form a hermetic friction fit with the first fitting 62. The cover 78, like the other parts of the regulator, is formed from a synthetic plastic. The thickness of the cover 78 preferably is so chosen that the cover can be deformed under manual pressure and will automatically restore itself to its molded shape upon release of such pressure, that is to say, the cover, as molded, is resilient but yet flexible. The skirt 82 of the cover is provided with a male thread for a purpose soon to be mentioned.

The fourth part of the regulator 18 is a diaphragm 84 which, like the other parts, is molded from plastic. The diaphragm is sufficiently thin to be resilient so that it can be flexed under pressure. The periphery of the diaphragm is thickened as indicated at 86 to enable it to be squeezed perpendicular to the general plane of the diaphragm without destroying the diaphragm. The diaphragm has a dependent central valve stem 88 the tip of which is conical.

The fifth, and last, part of the regulator 18 is a low pressure cup 90 having an open upper female threaded mouth 92 that is designed to be screwed onto the male threaded skirt 82 of the cover 78. The cup includes an annular shoulder 94 that is directly below the skirt 82, the thickened periphery 86 of the diaphragm being caught between said shoulder and the mouth of the skirt when the cover and cap are screwed together. Thus, the cup and cover jointly define a space which is subdivided by the diaphragm 84 and, as thus subdivided, constitutes a high pressure chamber 96 defined by the cover and diaphragm, and a low pressure chamber 98 defined by the cup and diaphragm. The cup includes an inlet 100 having a tapered tip which is hermetically frictionally engaged with the second outlet fitting 68. Hence, there is present in the high pressure chamber liquid under the high pressure at which it exits from the container 12, and in the low pressure chamber liquid under the low pressure caused by the throttling action of the valve seat 64 and valve stem 66. Due to this arrangement, the cup and cover provide a differential pressure across the diaphragm 84. The differential pressure urges the tip of the valve stem 88 toward a valve seat 102 leading to an outlet 104 for the regulator 18.

The high pressure chamber 96 is a dead-end chamber for the liquid medicament at high pressure, which is to say, the liquid medicament enters the chamber but has no place to flow from the chamber and is trapped therein. The liquid medicament in this chamber serves no medicinal purpose — it is simply there for regulative purposes. Any fluid under pressure would serve the same function. Indeed, when the device is placed into operation, fluid in the high pressure chamber may include both liquid medicament and air. This is not generally considered to be desirable, both for good regulation purposes and for avoidance of contamination of the liquid medicament. Hence, in the use of the regulator it is desirable to purge any gas that may be present in the high pressure chamber. Such purging can be accomplished in any desirable fashion. For instance, it may be accomplished by depressing the cover 78 so as to force air out of the inlet fitting 80 before connecting said inlet fitting to the first outlet fitting 62. Also, the high pressure chamber can be purged of gas by initially slightly loosening the connection between the cover and cup which will allow gas therein to flow out of the regulator. Preferably, this latter method of purging is assisted by arranging the cover vertically below the cup during the period of purging.

There is a further throttling action on the liquid medicament as it leaves through the outlet 104. This latter throttling action controls the rate of flow of the liquid medicament. By maintaining a proper pressure differential between the two chambers 96 and 98, the flow rate of liquid leaving the regulator 18 will be kept constant. When the flow increases beyond the predetermined rate, the pressure in the chamber 98 drops, tending to restrict flow of liquid through the exit throttle constituted by the valve stem 88 and the valve seat 102. On the other hand, if the flow of liquid through the outlet 104 falls below the desired rate of flow, the pressure of the liquid medicament in the low pressure chamber 90 will increase so as to lift the valve stem 88 and increase the rate of flow. By adjusting the control stem 74, a given differential in pressure is established between the high and low pressure chambers, subject, of course, to small variations as the valve stem 88 fluctuates in its position to maintain a constant output flow rate of the liquid medicament.

The alternate construction of regulator 18' shown in FIG. 4 has been included to show a self-purging regulator. Said regulator 18' includes a vessel 106 having an inlet 108 and an outlet 110. The vessel is transversely divided by a flexible resilient diaphragm 112. The diaphragm carries a valve stem 114 the tip of which is conical and cooperates with a valve seat 116 that leads to the outlet 110. In unbiased condition the tip of the valve stem is spaced from the valve seat, as is the tip of the valve stem 88 spaced from the valve seat 102 of the diaphragm 84 in the regulator 18. The diaphragm 112 separates the interior of the vessel 106 into a high pressure chamber 118 and a low pressure chamber 120. The two chambers are interconnected by a shunt 122 in which a throttle valve 124 is interposed. The flow of liquid medicament enters the high pressure chamber 118 under the high pressure at which the liquid in the container 12 is maintained. The liquid then flows through the shunt 122 into the low pressure chamber 120, the pressure of the liquid being reduced as it traverses the throttle valve 124. Thus, once again, as in the case of the regulator 18, a resilient diaphragm is located between a high pressure chamber and a low pressure chamber so that the differential pressure acts on the diaphragm and causes movement of a valve stem with respect to a valve seat. The regulator 18' functions to maintain constant flow in the same manner as the regulator 18 above described. However, in the regulator 18' the liquid medicament both enters and leaves the high pressure chamber and, hence, will purge from said chamber any gas that may be present. During purging, the regulator 18' is held so that the shunt 122 is uppermost until all of the gas has left the high pressure chamber. Then the regulator 18' is held so that the outlet 110 is uppermost, whereupon all the gas will leave the low pressure chamber.

After the liquid medicament leaves the regulator 18 (or 18'), flowing at a constant rate which is determined by the setting of the adjustable throttle valve associated with such regulator, the liquid enters the inlet 126 to a standard drip chamber 128. The drip chamber preferably is transparent so that the level of the liquid which accumulates at the lower half of the chamber can be observed as can the rate of drops falling into such body of liquid from the inlet 126. Liquid accumulates in the lower half of the drip chamber and leaves the drip chamber to enter the flow measuring device 24. Said flow measuring device is of conventional construction and is fully illustrated and described in U.S. Pat. No. 3,034,504.

In the flow measuring device the liquid medicament traverses a series of vertical passageways and interconnecting horizontal passageways. In the first vertical passageway the liquid medicament runs from a higher to a lower position; the liquid medicament also runs from a higher to a lower position in the last vertical passageway.

Figure 5:
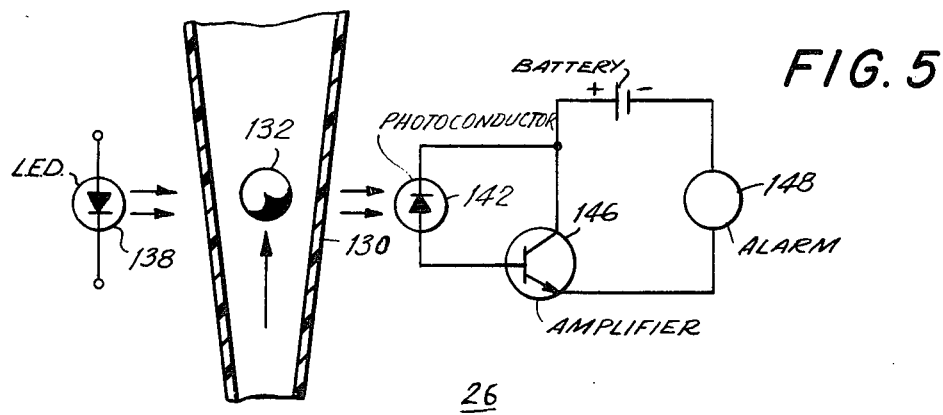
FIG. 5 is a fragmentary view of an alarm signaling mechanism the circuits for which are shown schematically, said mechanism being employed in conjunction with the flow measuring device.

In an intermediate vertical passageway 130 the liquid runs from a lower position to a high position. This passageway can be seen in FIGS. 1 and 5. Said passageway has a cross-section which increases from the bottom to the top. Disposed in the passageway is a flow indicating member 132 of spherical configuration the diameter of which is approximately equal to the diameter of the intermediate passageway 130 at the lower end thereof. As liquid medicament flows upwardly in the passageway 130, it exerts an upward pressure on the flow indicating member 132 which then assumes an equilibrium position in the passageway 130 that is a function of the rate of flow of the liquid medicament. Desirably, a flow scale 134 calibrated in any suitable units is located alongside the intermediate passageway. A convenient flow scale is graduated in liters per day. This will have a maximum range of from 0.1 to 10 liters per day, although a more convenient scale which will have a greater use and a greater accuracy because of the smaller range of the scale is from ½ to 5 liters per day. The provision of a flow measuring device greatly assists a hospital technician or nurse because it provides an instantaneous reading of flow rate of administration of a liquid medicament, in contrast to a visual observation of the drop rate in the drip chamber which can vary from moment to moment depending upon a large number of factors. These, however, will average out and not appear in the flow measuring device which does not experience a rapid fluctuation corresponding to small changes in flow rate; that is to say, the response of the flow measuring device damps small changes and presents an average reading.

The liquid medicament leaving the flow measuring device is led through a conduit 136 to the administration implement 20, here illustrated as a conventional hypodermic needle, which will be introduced subcutaneously for parenteral application to a patient, for example, in an intravenous mode or a perfusion mode. Mention has been made heretofore that the liquid can be any type which is employed for administration to a patient and is generically described simply as a medicament, although it does include liquids which, strictly speaking, are not medicines such, for instance, as saline solutions, glucose solutions, whole blood, blood fractions, etc.

Reference previously has been made to the safety valve 46. This, of course, is not needed if the gas bladder is charged with a carbon dioxide cartridge, the pressure and gas volume of which can be controlled to provide the desired pressure in the gas bladder at the beginning of administration of a liquid medicament. However, the safety valve is most desirable if a local source of oxygen under pressure, as in a hospital room, is employed. When the gas bladder is thus pressurized, because of the presence of the safety valve which is set to blow at the maximum pressure desired, the person using the device does not have to observe too closely how long a time high pressure oxygen is charged into the gas bladder. It previously has been indicated that a suitable pressure is 7 to 8 psig. However, depending upon the size of the gas bladder and the amount of liquid medicament provided in the container 12, usable results are secured at ranges from 5 to 10 psig in the gas bladder.

Mention also should be made of the fact that because the throttle valves in the regulators 18 and 18' are needle valves which are operated by rotating a threaded member, an extremely fine degree of control for the flow rate is obtained.

The regulator 18 has a safety feature which is quite desirable and which is not present in the regulator 18'. If the diaphragm 84 ruptures in the regulator 18, high pressure liquid can flow from the inlet 80 to the outlet 104, by-passing the throttling needle valve. If the full high pressure present in the liquid as it leaves the container 12 were permitted to be applied to a patient, particularly if the implement 20 were used in an intravenous mode, considerable damage could be done to the patient. The human body is not equipped to permit rapid injection of liquid under such a pressure or, indeed, rapid injection of any liquid such as would take place if the diaphragm 84 burst and no safety feature were provided. However, it will be observed that the passageway through the inlet 80 is small. The passageway acts as a choke or restriction which will prevent rapid flow of liquid from the inlet to the outlet 104 in the event of bursting of the diaphragm 84. Also, this small passageway will act as a throttle to reduce pressure of the liquid medicament. Normally, the fineness of the passageway in the inlet 80 will not affect proper operation of the regulator 18 because, as noted previously, the high pressure chamber 96 is a dead-end chamber, which is to say, that liquid does not flow through it but only to it. Once this chamber is filled, no liquid will enter it so that the passageway through the inlet 80 does not, except at the very beginning of operation of the regulator 18, experience a traversal of liquid therethrough. Hence, any pressure present at the inlet 52 will be present in the high pressure chamber 96.

The alarm signaling mechanism 26 is associated with the flow measuring device 24 and constitutes a light emitting diode 138 disposed to pass a beam through the passageway 130 and impinge on a photoconductor cell 142. The photoconductor cell 142 is in a circuit which connects the same through an amplifier 146 to an alarm 148. The alarm circuit will be activated only when an alarm condition exists, i.e. too slow or too rapid a rate of feed, thus prolonging the life of the power source which preferably is a battery.

It thus will be seen that there are provided devices which achieve the various objects of the invention and which are well adapted to meet the conditions of practical use.

As various possible embodiments might be made of the above invention, and as various changes might be made in the embodiments above set forth, it is to be understood that all matter herein described or shown in the accompanying drawings is to be interpreted as illustrative and not in a limiting sense.

Having thus described the invention there is claimed as new and desired to be secured by Letters Patent:

1. A constant flow rate liquid medicament administering device comprising:
   a. a container for a liquid medicament,
      i. said container having an outlet,
   b. means for pressurizing the liquid in the container,
   c. a constant flow rate throttling regulator having an inlet and an outlet,
   d. means connecting the container outlet to the regulator inlet;
   e. said regulator including means controlled as a function of the differential in the liquid pressures at the inlet and the outlet of the regulator and furnishing a throttled constant flow rate of liquid at the outlet of the regulator which is independent of the pressure of the liquid at the inlet and the outlet of the regulator,
   f. means for coupling the device to a patient, and
   g. means connecting the regulator outlet to the coupling means.

2. A device as set forth in claim 1 wherein the regulator includes a vessel subdivided by a single diaphragm into a high pressure chamber and a low pressure chamber, a throttle valve between the low pressure chamber and the regulator outlet, a kinematic connection between the diaphragm and the throttle valve, and a manually regulatable pressure reducing connection external to the vessel between the high pressure chamber and the low pressure chamber to selectively vary the constant flow rate of liquid medicament from the regulator.

3. A device as set forth in claim 2 wherein at least one wall of the high pressure chamber is sufficiently resilient to be deformed by manual pressure so as to assist in purging the high pressure chamber of gas prior to operation of the device.

4. A device as set forth in claim 2 wherein introduction of liquid medicament under pressure to the high pressure chamber of the regulator is dead-ended at said high pressure chamber.

5. A device as set forth in claim 2 wherein liquid medicament introduced into the high pressure chamber leaves the high pressure chamber to the external connection so that the regulator is self-purging.

6. A device as set forth in claim 2 wherein a restricted flow passageway is provided at an inlet to the high pressure chamber to prevent rapid flow of liquid medicament through the regulator in the event that the diaphragm ruptures.

* * * * *